United States Patent
Becker et al.

(10) Patent No.: US 9,321,711 B2
(45) Date of Patent: Apr. 26, 2016

(54) SYSTEM AND PROCESS FOR MAKING PHENOL AND/OR CYCLOHEXANONE

(71) Applicant: ExxonMobil Chemical Patents Inc., Baytown, TX (US)

(72) Inventors: Christopher L. Becker, Manhattan, KS (US); James R. Lattner, LaPorte, TX (US); Francisco M. Benitez, Cypress, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/763,471

(22) PCT Filed: Feb. 21, 2014

(86) PCT No.: PCT/US2014/017693
§ 371 (c)(1),
(2) Date: Jul. 24, 2015

(87) PCT Pub. No.: WO2014/137623
PCT Pub. Date: Sep. 12, 2014

(65) Prior Publication Data
US 2015/0353459 A1    Dec. 10, 2015

Related U.S. Application Data

(60) Provisional application No. 61/772,444, filed on Mar. 4, 2013.

(30) Foreign Application Priority Data

May 7, 2013    (EP) .................................. 13166816

(51) Int. Cl.
*C07C 45/53*    (2006.01)
*C07C 37/08*    (2006.01)
*C07C 2/66*    (2006.01)
*B01J 19/00*    (2006.01)
*C07C 409/14*    (2006.01)
*B01J 19/24*    (2006.01)
*B01D 3/14*    (2006.01)
*C07C 37/74*    (2006.01)
*C07C 45/82*    (2006.01)

(52) U.S. Cl.
CPC ................ *C07C 37/08* (2013.01); *B01D 3/143* (2013.01); *B01J 19/245* (2013.01); *C07C 37/74* (2013.01); *C07C 45/53* (2013.01); *C07C 45/82* (2013.01); *C07C 409/14* (2013.01); *B01J 2219/00006* (2013.01); *B01J 2219/24* (2013.01); *C07C 2101/14* (2013.01)

(58) Field of Classification Search
CPC ........ C07C 45/53; C07C 45/82; C07C 37/08; C07C 2/66; B01J 2219/00; B01J 19/00
USPC .................... 568/342, 798; 585/467; 422/187
See application file for complete search history.

(56) References Cited

U.S. PATENT DOCUMENTS

| 4,230,638 | A | 10/1980 | Murtha |
| 4,306,944 | A | 12/1981 | Murthy et al. |
| 6,037,513 | A | 3/2000 | Chang et al. |
| 6,720,462 | B2 | 4/2004 | Kuhnle et al. |

FOREIGN PATENT DOCUMENTS

| WO | 2009/131769 | 10/2009 |
| WO | 2011/001244 | 1/2011 |
| WO | 2011/100013 | 8/2011 |

*Primary Examiner* — Sikarl Witherspoon
(74) *Attorney, Agent, or Firm* — Siwen Chen; Stephen A. Baehl

(57) ABSTRACT

A system for producing high-purity phenol and/or cyclohexanone from cyclohexylbenzene oxidation includes a cyclohexylbenzene feed hydrogenation reactor, a bubble column oxidation reactor, a cyclohexylbenzene hydroperoxide concentrator, a cleavage reactor, and a separation and purification sub-system. The components and the integrated system are designed such that high-purity phenol and/or cyclohexanone can be produced at high energy efficiency.

23 Claims, 2 Drawing Sheets

SYSTEM AND PROCESS FOR MAKING PHENOL AND/OR CYCLOHEXANONE

PRIORITY CLAIM TO RELATED APPLICATIONS

This application is a National Stage Application of International Application No. PCT/US2014/017693 filed Feb. 21, 2014, which claims priority to U.S. Provisional Application Ser. No. 61/772,444 filed Mar. 4, 2013, and European Application No. 13166816.2 filed May 7, 2013, the disclosures of which are fully incorporated herein by their reference.

FIELD

The present invention relates to systems and processes for making phenol and/or cyclohexanone. In particular, the present invention relates to systems and processes for making phenol and/or cyclohexanone from cyclohexylbenzene. The present invention is useful, e.g., in making high-purity cyclohexanone and phenol materials starting from benzene and hydrogen.

BACKGROUND

The production of phenol from cyclohexylbenzene is an emerging technology, interesting in that it co-produces cyclohexanone, rather than acetone. Cyclohexylbenzene may be produced, for example, by direct alkylation of benzene with cyclohexene, or as disclosed in U.S. Pat. No. 6,037,513, by contacting benzene with hydrogen in the presence of a catalyst. The cyclohexylbenzene may then be oxidized to the corresponding hydroperoxide and the hydroperoxide cleaved to phenol and cyclohexanone using a catalyst.

The production of phenol and cyclohexanone from cyclohexylbenzene also produces various contaminants that are difficult to separate from the desired products. However, the nature of those contaminants and the separations thereof are significantly different from those in the conventional Hock process for the production of phenol and acetone, and/or the conventional cyclohexanone production from cyclohexane or phenol. For example, hydroalkylation of benzene produces significant amounts of, among others, cyclohexane and lesser amounts of methylcyclopentane, cyclohexene, phenylcyclohexene, and phenylcyclohexyldiene. Similarly, the oxidation of cyclohexylbenzene typically produces peroxide species alien to the Hock process, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide and cyclohexyl-1-phenyl-4-hydroperoxide. The cleavage of these various hydroperoxides produces a wide variety of contaminant species which are not produced by the chemistry and technology of either the Hock process, the cyclohexane oxidation process, or the phenol hydrogenation process. The yields and energy efficiency in the oxidation, cleavage and separation steps determine the final cost and quality of the phenol and cyclohexanone product.

The contaminants in the phenol product can significantly impact the quality of products made from phenol, such as bis-phenol A, polycarbonates, phenolic resins, and the like.

Cyclohexanone is widely used to make caprolactam, which, in turn, is used for making nylon-6, a widely used polymer material. The purity of caprolactam has significant impact on the quality such as strength of nylon-6 made therefrom. For example, in various industrial processes for making cyclohexanone, methylcyclopentanone may be produced as a contaminant. Even at a very small amount, methylcyclopentanone may lead to the formation of highly undesirable contaminants, particularly methylvalerolactams, which is very difficult to remove from caprolactam. The various isomers of methylvalerolactam, by polymerization with each other and/or with caprolactam, may significantly reduce the quality and performance of the nylon-6 product, even at a low concentration.

As such, there is a strong need of a system for making high purity phenol and cyclohexanone at high yields in the oxidation, cleavage and separation steps, desirably with high energy efficiency.

SUMMARY

The present inventors have found that by carefully designing a system comprising a cyclohexylbenzene feed pretreatment unit, an oxidization device, a cyclohexylbenzene concentrator, a cleavage reactor, and a separation and purification sub-system comprising fractionation columns and the overall integration among these components, very high overall yields of phenol and cyclohexanone can be achieved with high energy efficiency via the cyclohexylbenzene oxidation route.

One aspect of the present disclosure relates to a system for producing phenol and/or cyclohexanone from cyclohexylbenzene, the system comprising:

(A) a hydrogenation reactor comprising a bed of hydrogenation catalyst, configured to receive a cyclohexylbenzene feed comprising an olefin and hydrogen and to produce a hydrogenation effluent with a reduced concentration of the olefin compared to the feed;

(B) a separation drum in fluid communication with the hydrogenation reactor configured to receive at least a portion of the hydrogenation effluent and to produce a lower drum effluent consisting essentially of a liquid, and an upper drum effluent consisting essentially of a gas;

(C) an oxidizing device comprising at least one bubble column reactor in fluid communication with the separation drum configured to receive (i) at least a portion of the lower drum effluent, (ii) a stream of $O_2$-containing gas fed into the bubble column reactor at a location in the vicinity of the bottom thereof, and (iii) a cyclic imide catalyst, and to produce a lower oxidation effluent comprising cyclohexylbenzene and cyclohexylbenzene hydroperoxide and an upper oxidation effluent;

(D) a concentrator configured to operate under an absolute internal pressure of Pcon, where 133 Pa≤Pcon≤6666 Pa, in fluid communication with the oxidizing device configured to receive at least a portion of the lower oxidation effluent and to produce a lower concentrator effluent comprising at least 30 wt % of cyclohexylbenzene hydroperoxide, the percentage based on the total weight of the lower concentrator effluent, and an upper concentrator effluent comprising at least 50 wt % of cyclohexylbenzene, the percentage based on the total weight of the upper concentrator effluent;

(E) a cleavage reactor comprising a vessel configured to receive (i) at least a portion of the cyclohexylbenzene hydroperoxide in the lower concentrator effluent and (ii) a cleavage catalyst and to produce a cleavage reaction effluent comprising phenol, cyclohexanone, and cyclohexylbenzene.

A second aspect of the present disclosure relates to a system for making phenol and/or cyclohexanone, comprising:
a system according to the first aspect above, and
(1) a first fractionation column configured to receive at least a portion of the cleavage reaction mixture comprising phenol, cyclohexanone, cyclohexylbenzene, and water to produce a first lower effluent comprising the amine salt, and a first upper effluent comprising phenol, cyclohexanone and water;

(2) a second fractionation column in fluid communication with the first fractionation column configured to receive at least a portion of the first upper effluent to produce a second lower effluent comprising phenol and cyclohexanone, and a second upper effluent comprising water;

(3) a third fractionation column in fluid communication with the second fraction column configured to receive at least a portion of the second lower effluent and an extractive solvent to produce a third lower effluent comprising phenol and the extractive solvent, and a third upper effluent comprising at least 60 wt % of cyclohexanone, the percentage based on the total weight of the third upper effluent;

(4) an optional fourth fractionation column in fluid communication with the third fractionation column configured to receive at least a portion of the third upper effluent to produce a fourth lower effluent comprising components having normal boiling points higher than that of cyclohexanone, and a fourth upper effluent comprising at least 90 wt % cyclohexanone, the percentage based on the total weight of the fourth upper effluent;

(5) a fifth fractionation column in fluid communication with the third fractionation column configured to receive at least a portion of the third lower effluent to produce a fifth lower effluent comprising the extractive solvent, and a fifth upper effluent comprising at least 60 wt % of phenol, the percentage based on the total weight of the fifth upper effluent; and (6) a sixth fractionation column in fluid communication with the fifth fractionation column configured to receive at least a portion of the fifth upper effluent to produce a sixth bottom effluent comprising cyclohexylbenzene, and a sixth upper effluent comprising at least 90 wt % of phenol, the percentage based on the total weight of the sixth upper effluent.

A third aspect of the present disclosure relates to a process for making phenol and/or cyclohexanone, using a system according to the first aspect or the second aspect above.

DETAILED DESCRIPTION OF THE EMBODIMENTS

Figure 1A:
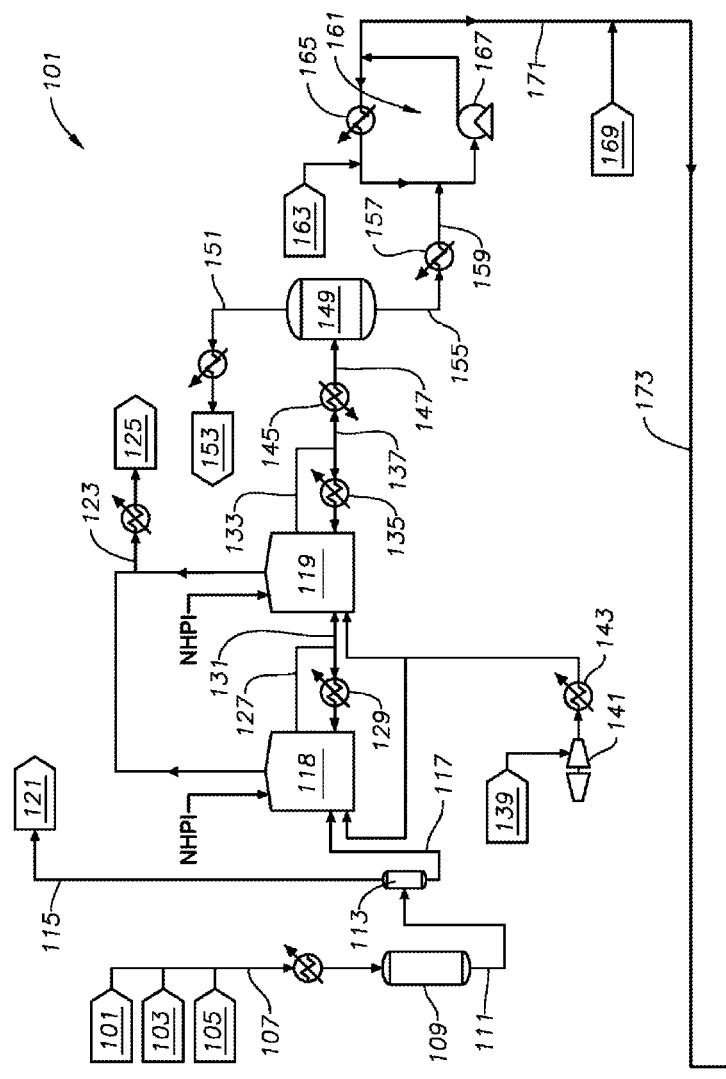
FIGS. 1A and 1B are schematic flow diagrams illustrating an embodiment of the system according to the present disclosure for producing high-purity phenol and/or cyclohexanone from cyclohexylbenzene.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a C12+ component" should be interpreted to include one, two or more C12+ components unless specified or indicated by the context to mean only one specific C12+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

In the present disclosure, a location "in the vicinity of" an end (top or bottom) of a column means a location within a distance of a*Hc from the end (top or bottom) of the column, where Hc is the height of the column from the bottom to the top, and a1≤a≤a2, where a1 and a2 can be, independently, 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, as long as a1<a2. For example, a location in the vicinity of an end of a column can have an absolute distance from the end (top or bottom) of at most D meters, where D can be 5.0, 4.5, 4.0, 3.5, 3.0, 2.5, 2.0, 1.5, 1.0, 0.8, 0.5, 0.4, 0.3, 0.2, 0.1, or 0.

An "upper effluent" as used herein may be at the very top or the side of a vessel such as a fractionation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the generic term "dicylcohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, diicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

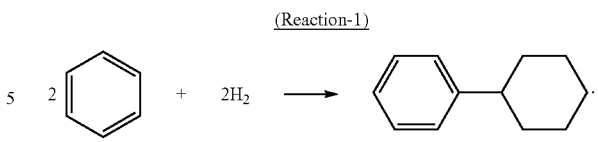

Alternatively, cyclohexylbenzene can be produced by direct alkylation of benzene with cyclohexene in the presence of a solid-acid catalyst such as molecular sieves in the MCM-22 family according to the following Reaction-2:

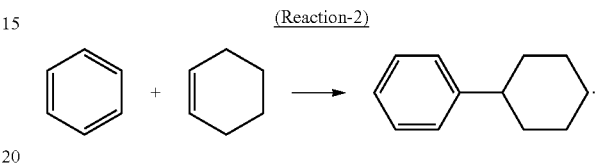

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b)

dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 $hr^{-1}$ to 10 $hr^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

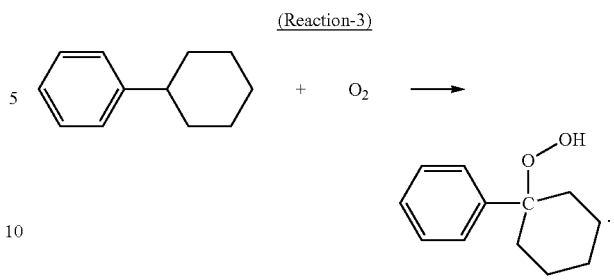

In exemplary processes, the oxidizing step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

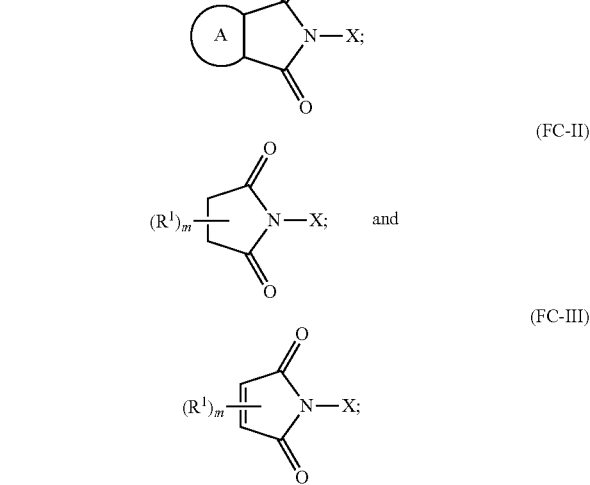

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

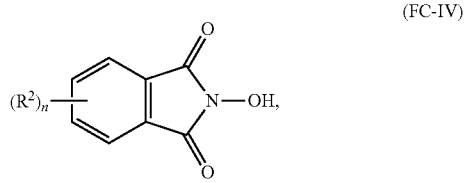

(FC-IV)

where:

R², the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

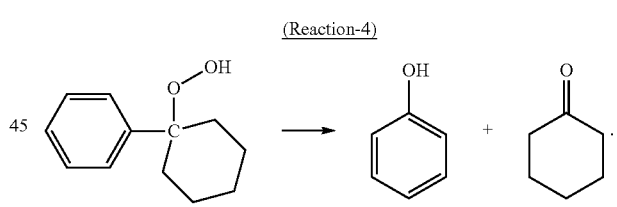

(Reaction-4)

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction preferably occurs under cleavage conditions including a temperature in a range from 20° C. to 200° C., or from 40° C. to 120° C., and a pressure in a range from 1 to 370 psig (at least 7 kPa, gauge and no greater than 2,550 kPa, gauge), or from 14.5 psig to 145 psig (from 100 kPa, gauge to 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cad<Cac2. Preferably, Cad is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least AA wt %, where AA can be 90.0, 91.0, 92.0, 93.0, 94.0, 95.0, 96.0, 97.0, 98.0, 99.0, 99.5, 99.9, or even 100, the percentage based on the weight of a given hydroperoxide, or of all hydroperoxides fed to the cleavage step. This is desirable because any hydroperoxide, even the cyclohexyl-1-phenyl-1-hydroperoxide, becomes a contaminant in the downstream processes.

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first fractionation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent fractionation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

DESCRIPTION ACCORDING TO THE DRAWINGS

Figure 1B:
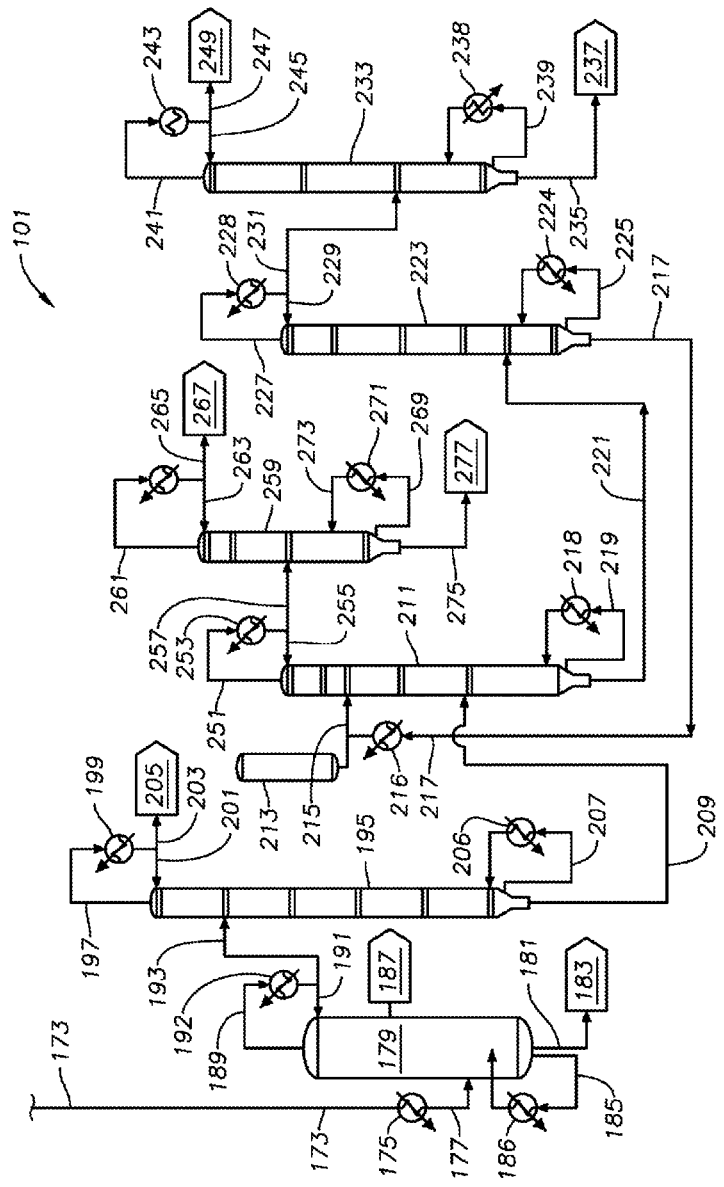

Referring to FIGS. 1A and 1B, in a system 101 for making phenol and cyclohexanone from cyclohexylbenzene, a fresh cyclohexylbenzene source 101, a recycle cyclohexylbenzene source 103 and a hydrogen source 105 provide a combined feed stream 107, which is heated and then supplied into a hydrogenation reactor 109, where olefin contaminants are converted into compounds with higher degree of saturation. As described below, the recycle cyclohexylbenzene stream 103 is prone to containing cyclohexenylbenzenes, which are converted into cyclohexylbenzene in reactor 109 as follows:

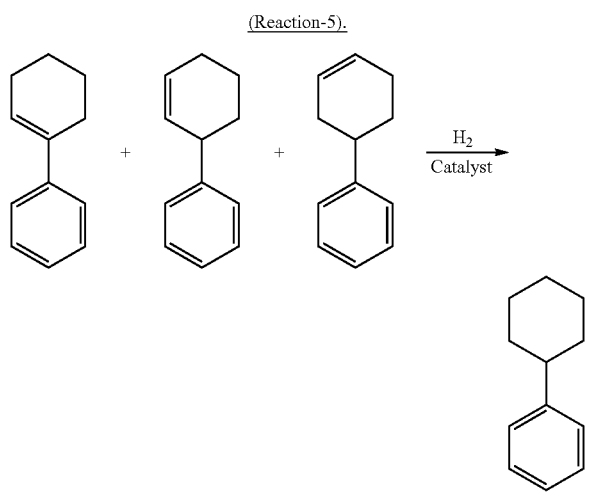

(Reaction-5).

The catalyst used in reactor 109 can be a fixed bed of catalyst comprising a Group 9 or Group 10 metal in the Periodic Table such as Ru, Rh, Pd, Os, Ir, and/or Pt supported on an inorganic substrate such as $Al_2O_3$ and/or $SiO_2$. The lower hydrogenation effluent 111 exiting reactor 109 is then fed into a separation drum 113 to obtain an upper drum effluent consisting essentially of a gas mixture comprising hydrogen, which may be cleaned and recycled to a step which requires hydrogen, or sent to a combustor 121, where it is combusted to provide heat needed in many steps in the process of the present disclosure, or other processes in the same facility.

The lower drum effluent, 117, consisting essentially of liquid cyclohexylbenzene and minor amounts of contaminants, is then fed into a first bubble column reactor 118, where cyclohexylbenzene is oxidized by $O_2$ contained in air bubbles supplied at the bottom of the reactor. NHPI, the oxidation reaction catalyst, is added into the reaction medium in the reactor. A side stream 127 of the reaction medium is taken, partly cooled by a heat exchanger 129 and then recycled back to reactor 118 such that the temperature of the reaction medium inside reactor 118 is maintained in the range from 60° C. to 150° C., or from 70° C. to 140° C., or from 80° C. to 120° C., or from 90 to 110° C. A stream 131 drawn from reactor 118 is then sent to a second bubble column reactor 119. Additional NHPI catalyst is added to reactor 119 to compensate the loss of some of the catalyst in the first reactor 118, and to increase the overall NHPI concentration to a level higher than in reactor 118. Cyclohexylbenzene remaining in stream 131 is further reacted with $O_2$ in air bubbles supplied in the vicinity of the bottom of reactor 119. Likewise, a side stream 133 is taken from reactor 119, which is partly cooled by heat exchanger 135 and recycled back to reactor 119 to control the temperature inside reactor 119 to a level similar to inside reactor 118, and partly delivered as stream 137 fed to a concentrator 149. Air from source 139 is supplied by a compressor 141, cooled by a heat exchanger 143 to remove moisture, and then fed to the bottoms of reactors 118 and 119 to generate the bubbles. The exhaust gas from the top of reactors 118 and 119 are collected as a stream, cooled by a heat exchanger 123 to remove water and cyclohexylbenzene, and then delivered to a pollution abatement system 125 for further treatment. Alternatively (not shown), between the bubble columns 117 and 119, one or more similarly equipped bubble columns may be situated, such that the oxidation assembly comprising all the bubble columns collectively achieve a desirable level of cyclohexylbenzene conversion and cyclohexylbenzene hydroperoxide selectivity.

Concentrator 149 operates at a low internal absolute pressure (i.e., a high vacuum) in the range from 133 Pa to 6666 Pa (such as from 150 Pa to 5000 Pa, or from 200 Pa to 3000 Pa, or from 300 Pa to 1000 Pa), such that the high boiling point cyclohexylbenzene is partly removed as an upper concentrator effluent 151, which is then cooled by a heat exchanger, and sent to a processing station 153 before recycled as part of the recycle cyclohexylbenzene source 103 to hydrogenation reactor 109. Concentrator 149 may comprise a falling film evaporator comprising a heat exchanger 145 which provides heat required for evaporation. A lower concentrator effluent 155 with a high concentration of cyclohexylbenzene hydroperoxide of at least 30 wt %, such as at least 40 wt %, or at least 50 wt %, or at least 60 wt %, or at least 70 wt %, or even as high as 80 wt %, may be obtained.

The concentrated cyclohexylbenzene hydroperoxide stream 155 is then cooled by a heat exchanger 157 and delivered to a cleavage reactor 161 to which sulfuric acid catalyst 163 is added. Reactor 161 comprises a heat exchanger 165 for extracting heat from the reaction medium thus maintaining the temperature at a desirably low level, such as in a range from 15° C. to 90° C., or from 20° C. to 80° C., or from 25° C. to 75° C., or from 30° C. to 70° C. A portion of the cleavage reaction medium is recycled via a pump 167, and a portion exits the cleavage reactor as a cleavage effluent stream 171, to which a neutralizing agent, such as an organic amine (e.g., methylamine, methylene diamine, propylene diamine, butylene diamine, and the like), is added from source 169, to react with the sulfuric acid catalyst to form an amine salt, thereby obtaining a neutralized effluent mixture stream 173.

Next, stream 173 is then heated by a heat exchanger 175 to become stream 177, which is sent to a first fractionation column 179 operating at an internal absolute pressure below 100 kPa, where three streams are produced: (i) a first lower effluent 181 comprising high-boiling point components including the amine salt, C12 oxygenates, and the like, which are purged at station 183; (ii) a first middle effluent comprising a high concentration of cyclohexylbenzene, which may be processed at station 187 and then become part of the recycle cyclohexylbenzene source 103 fed to hydrogenation reactor 109; and (iii) a first upper effluent 193 comprising phenol, cyclohexanone and water. A first reboiler 186 provides heat to column 179, and a condenser 192 provides cooling to a stream 189 withdrawn in the vicinity of the top thereof which is partly recycled as reflux stream 191, and partly as the first upper effluent 193 delivered to the second fractionation column 195. Column 179 has a minimum temperature in the vicinity of the top thereof Tmin1 and a maximum temperature in the vicinity of the bottom thereof Tmax1. The first lower effluent may comprise the amine salt at a concentration from A1 wt % to A2 wt %, where A1 and A2 can be, independently, 40, 45, 50, 55, 60, 70, 75, 80, 85, 90, 95, as long as A1<A2. The first middle effluent may comprise cyclohexylbenzene at a concentration from B1 wt % to B2 wt %, where B1 and B2 can be, independently, 40, 45, 50, 55, 60, 70, 75, 80, 85, 90, 91, 92, 93, 94, 95, 96, 97, 98, 99, as long as B1<B2.

The second fractionation column 195 produces (i) a second upper effluent 203 comprising light components such as water, which is sent to a station 205 for processing; and (ii) a second lower effluent 209 comprising phenol and cyclohexanone. A reboiler 206 heats a recycle stream 207 taken in the vicinity of the bottom of column 195 and thereby provides heat for column 195. A second condenser 199 at the top cools a stream 197 taken in the vicinity of the top of column 195, which is partly recycled to the column as a recycle stream 201 and partly delivered as a light stream 203 to station 205. Column 199 has a minimum temperature in the vicinity of the top thereof Tmin2 and a maximum temperature in the vicinity of the bottom thereof Tmax2.

The second lower effluent 209 is then delivered to a third fractionation column 211 which also receives a stream 215 of an extractive solvent such as diethylene glycol as a feed from source 213. Advantageously, stream 215 is fed at a location higher than the stream 209 on column 211. Advantageously, stream 215 is a combination of fresh extractive solvent form source 213 and a recycle extractive solvent stream 217. Column 211 produces a third upper effluent 257 comprising more than 50 wt % of cyclohexanone, and a third lower effluent 221 comprising phenol and the extractive solvent. Likewise, a third reboiler 218 heats a recycle stream 219 taken in the vicinity of the bottom and thereby provides heat for column 211. A condenser 253 at the top cools a stream 251 taken in the vicinity of the top of column 211, which is partly recycled to the column as a recycle stream 255 and partly delivered to the fourth fractionation column 259 as raw cyclohexanone stream 257. Column 211 has a minimum temperature in the vicinity of the top thereof Tmin3 and a maximum temperature in the vicinity of the bottom thereof Tmax3.

The fourth fractionation column 259 serves to purify the raw cyclohexanone stream 257. From this column, a fourth lower effluent 275 withdrawn in the vicinity of the bottom is delivered to storage tank 277, and then at least partly recycled to the first fractionation column 179, and an fourth upper effluent 265 comprising high-purity cyclohexanone is delivered to a storage tank 267. Likewise, a fourth reboiler 271 heats a recycle stream 269 taken in the vicinity of the bottom and thereby provides heat for column 259. A condenser at the top cools a stream 261 taken in the vicinity of the top of column 259, which is then partly recycled to the column as a recycle stream 263 and partly delivered to storage tank 267 as high-purity cyclohexanone stream 265. Column 259 has a minimum temperature in the vicinity of the top thereof Tmin4 and a maximum temperature in the vicinity of the bottom thereof Tmax4.

The fifth fractionation column 223 serves to separate the extractive solvent from phenol in stream 221 supplied from the third fractionation column 211. From this column, a fifth lower effluent 217 withdrawn in the vicinity of the bottom, comprising at least 40 wt % of the extractive solvent (the percentage based on the total weight of stream 217), is cooled by a heat exchanger 216, and then recycled to the third fractionation column 211 as part of the extractive solvent feed stream 215, and a fifth upper effluent 231 comprising raw phenol is delivered to the sixth fractionation column 233 as feed thereto. Likewise, a fifth reboiler 224 heats a recycle stream 225 taken in the vicinity of the bottom and thereby provides heat for column 223. A condenser 228 at the top cools a stream 227 taken in the vicinity of the top of column 223 which is then partly recycled to the column as a recycle stream 229 and partly delivered to the column 233 as raw phenol stream 231. Column 223 has a minimum temperature in the vicinity of the top thereof Tmin5 and a maximum temperature in the vicinity of the bottom thereof Tmax5.

The sixth fractionation column 233 serves to purify the raw phenol stream 231. From this column, a sixth lower effluent 235 withdrawn in the vicinity of the bottom is sent to station 237, optionally processed and then recycled to the first fractionation column 179 as a feed thereto (not shown), and a sixth upper effluent 247 comprising high-purity phenol is delivered to a storage tank 249. Likewise, a sixth reboiler 238 heats a recycle stream 239 taken in the vicinity of the bottom and thereby provides heat for column 233. A condenser 243 at the top cools a stream 241 taken in the vicinity of the top of column 233, which is then partly recycled to the column as a recycle stream 245 and partly delivered to storage tank 249 as high-purity phenol stream 247 (the sixth upper stream). Alternatively, the whole stream 241 is recycled after being cooled by heat exchanger 243, and a high purity phenol stream (the sixth upper stream) may be taken separately at a location in the vicinity of the top of column 233 below the location where the recycle stream 241 is taken. Column 233 has a minimum temperature in the vicinity of the top thereof Tmin6 and a maximum temperature in the vicinity of the bottom thereof Tmax6.

As an alternative (not shown) to the example shown in FIGS. 1A and 1B, in the system, the first fractionation column 179 produces, instead of three effluents, only two effluents: (a) a first lower effluent comprising high-boiling point components including the amine salt, C12 oxygenates, and cyclohexylbenzene; and (b) a first upper effluent 193 comprising phenol, cyclohexanone and water. The first upper effluent is then processed substantially in the same manner as in FIGS. 1A and 1B. The first lower effluent is then fed into a seventh fractionation column to produce a seventh upper effluent comprising cyclohexylbenzene, and a seventh lower effluent comprising the amine salt. The seventh upper effluent is then processed similar to the first middle effluent shown in FIGS. 1A and 1B. the seventh fractionation column has a minimum temperature in the vicinity of the top thereof Tmin7 and a maximum temperature in the vicinity of the bottom thereof Tmax7. Compared to the example of FIGS. 1A and 1B, this alternative system uses one more fractionation column, but will achieve higher purity of the first upper effluent and a higher purity of the cyclohexylbenzene stream. The latter can then be recycled to a previous step such as hydrogenation and/or oxidation with less treatment required. The seventh lower effluent may comprise the amine salt at a concentration from A3 wt % to A4 wt %, where A3 and A4 can be, independently, 45, 50, 55, 60, 70, 75, 80, 85, 90, 95, as long as A3<A4. The seventh upper effluent may comprise cyclohexylbenzene at a concentration from B3 wt % to B4 wt %, where B3 and B4 can be, independently, 40, 45, 50, 55, 60, 70, 75, 80, 85, 90, 95, as long as B3<B4.

Desirably, at least one, two, three, four, five, and up to all of the following conditions is met in system 101:
  (i) 180° C.≤Tmax1≤300° C.;
  (ii) 80° C.≤Tmin1≤150° C.;
  (iii) 80° C.≤Tmax2≤180° C.;
  (iv) 40° C.≤Tmin2≤100° C.;
  (v) 120° C.≤Tmax3≤220° C.;
  (vi) 50° C.≤Tmin3≤150° C.;
  (vii) 120° C.≤Tmax4≤300° C.;
  (viii) 150° C.≤Tmin4≤250° C.;
  (ix) 120° C.≤Tmax5≤250° C.;
  (x) 80° C.≤Tmin5≤180° C.;
  (xi) 150° C.≤Tmax6≤300° C.;
  (xii) 120° C.≤Tmin6≤250° C.;
  (xiii) 150° C.≤Tmax7≤400° C.; and
  (xiv) 120° C.≤Tmin7≤300° C.

Desirably, in system 101, at least one, two, three or all of the following conditions is met:
  (i) Tmin6>Tmax3;
  (ii) Tmin6>Tmax5;
  (iii) Tmin6>Tmax2; and
  (iv) Tmin7>Tmax2.

Even more desirably, in system 101, at least one, two or three of the following conditions is met:
  (i) Tmax1>Tmax6>Tmax5>Tmax3>Tmax2;
  (ii) Tmax1>Tmax4; and
  (iii) Tmax1>Tmax6.

Desirably, the temperature profile of the various vessels and columns are selected such that at least one, two, three, and up to all of the first, second, third, fourth, fifth, sixth and seventh upper effluents provides heat to a fluid fed into an upstream fractionation column. Specifically, at least one, two, three or four of the following conditions is met:
  (i) a stream taken from a location in the vicinity of the top of the six fractionation column provides heat to a fluid fed into the third fractionation column;
  (ii) a stream taken from a location in the vicinity of the top of the six fractionation column provides heat to a fluid fed into the fifth fractionation column;
  (iii) a stream taken from a location in the vicinity of the top of the six fractionation column provides heat to a fluid fed into the first fractionation column; and
  (iv) a stream taken from a location in the vicinity of the top of the fourth fractionation column provides heat to a fluid fed into the first fractionation column.

Desirably, at least one, two, three or four of the following conditions is met:
  (i) a stream taken from a location in the vicinity of the top of the six fractionation column provides heat to a fluid fed into the third fractionation column via the third reboiler;
  (ii) a stream taken from a location in the vicinity of the top of the six fractionation column provides heat to a fluid fed into the fifth fractionation column via the fifth reboiler;
  (iii) a stream taken from a location in the vicinity of the top of the six fractionation column provides heat to the reaction mixture fed into the first fractionation column; and
  (iv) a stream taken from a location in the vicinity of the top of the fourth fractionation column provides heat to the reaction mixture fed into the first fractionation column.

Using one material stream to heat or cool another stream in the process significantly improves the energy efficiency of the system. To ensure successful distillation and separation, and to achieve the above temperature profiles, it is highly desirable that the absolute pressures inside the first fractionation column 179, the second fractionation column 195, the third fractionation column 211, and the fifth fractionation column 223 are below 100 kPa, and/or the absolute pressures inside the fourth fractionation column 259 and the sixth fractionation column 233 are higher than 100 kPa.

The present disclosure includes, among others, the following non-limiting aspects and/or embodiments:

I1. A system for producing phenol and cyclohexanone from cyclohexylbenzene, the system comprising:
  (I-1A) a hydrogenation reactor comprising a bed of hydrogenation catalyst, configured to receive a cyclohexylbenzene feed comprising an olefin and hydrogen and to produce a hydrogenation effluent with a reduced concentration of the olefin compared to the feed;
  (I-1B) a separation drum in fluid communication with the hydrogenation reactor configured to receive at least a portion of the hydrogenation effluent and to produce a lower drum effluent consisting essentially of a liquid, and an upper drum effluent consisting essentially of a gas;
  (I-1C) an oxidizing device comprising at least one bubble column reactor in fluid communication with the separation drum configured to receive (i) at least a portion of the lower drum effluent, (ii) a stream of $O_2$-containing gas fed into the bubble column reactor at a location in the vicinity of the bottom thereof, and (iii) a cyclic imide catalyst, and to produce a lower oxidation effluent comprising cyclohexylbenzene and cyclohexylbenzene hydroperoxide and an upper oxidation effluent;
  (I-1D) a concentrator configured to operate under an absolute internal pressure of Pcon, where 133 Pa≤Pcon≤6666 Pa, in fluid communication with the oxidizing device configured to receive at least a portion of the lower oxidation effluent and to produce a lower concentrator effluent comprising at least 30 wt % of cyclohexylbenzene hydroperoxide, the percentage based on the total weight of the lower concentrator effluent, and an upper concentrator effluent comprising at least 50 wt % of cyclohexylbenzene, the percentage based on the total weight of the upper concentrator effluent;
  (I-1E) a cleavage reactor comprising a vessel configured to receive (i) at least a portion of the cyclohexylbenzene hydroperoxide in the lower concentrator effluent and (ii) a cleavage catalyst and to produce a cleavage reaction effluent comprising phenol, cyclohexanone, and cyclohexylbenzene.

I-2. The system of I-1, the system further comprising:
  (I-1F) a first fractionation column configured to separate at least a portion of the cyclohexylbenzene in the cleavage reaction effluent further in fluid communication with the hydrogenation reactor by which at least a portion of the separated cyclohexylbenzene is recycled to the hydrogenation reactor.

I-3. The system of I-1 or I-2, wherein the concentrator is in further fluid communication with the hydrogenation reactor through which at least a portion of the cyclohexylbenzene in the upper concentrator effluent is recycled to the hydrogenation reactor.

I-4. The system of any of I-1 to I-3, wherein the hydrogenation catalyst comprises a support and a Group 9 or Group 10 metal, such as a metal selected from Ru, Rh, Pd, Os, Ir, Pt and mixtures and combinations thereof.

I-5. The system of any of I-1 to I-4, wherein the oxidizing device comprises at least two bubble column reactors connected in series.

I-6. The system of I-5, wherein the oxidizing device comprises at least three bubble column reactors connected in series.

I-7. The system of any of I-1 to I-6, wherein at least one of the bubble column reactor comprises a cooling loop which draws a stream of the oxidation reaction medium from the bubble column reactor, cools at least a portion of the stream of oxidation reaction medium and recycles at least a portion of the cooled portion to the bubble column, thereby maintaining the temperature of the reaction medium inside the bubble column inside a temperature range from 50° C. to 150° C.

I-8. The system of any of I-1 to I-7, wherein the separation drum is in further fluid communication with a combustor through which at least a portion of the upper drum effluent is sent to the combustor.

I-9. The system of any of I-1 to I-8, wherein the hydrogenation reactor is configured to operate at a temperature of Thr and a pressure Phr, where 50° C.≤Thr≤150° C., and 150 kPa≤Phr≤1850 kPa.

I-10. The system of any of I-1 to I-9, wherein the separation drum is configured to operate at a temperature of Tsd, where 50° C.≤Tsd≤150° C.

I-11. The system of I-10, wherein the separation drum is configured to operate at a temperature no less than Thr−20° C., where Thr is the operating temperature of the hydrogenation reactor.

I-12. The system of any of I-1 to I-11, wherein the concentrator is configured to operate at a temperature of Tcon, where 50° C.≤Tcon≤150° C.

I-13. The system of any of I-1 to I-12, where the concentrator comprises a falling film evaporator.

I-14. The system of any of I-1 to I-13, wherein the concentrator comprises a heater for heating the fluid inside the concentrator.

I-15. The system of any of I-1 to I-14, wherein the concentrator is in further fluid communication with the hydrogenation reactor through which at least a portion of the cyclohexylbenzene in the upper concentrator effluent is recycled to the hydrogenation reactor.

I-16. The system of any of I-2 to I-15, wherein:
the cleavage catalyst comprises a liquid acid;
the system further comprises, between the cleavage reactor and the first fractionation column, a neutralization reactor configured to receive at least a portion of the cleavage reaction effluent and a base and to produce a cleavage reaction mixture having a reduced concentration of the cleavage catalyst compared to the cleavage reactor effluent,
at least a portion of the cleavage reaction mixture is fed into the first fractionation column.

I-17. The system of I-16, wherein the cleavage catalyst comprises concentrated sulfuric acid and water, and the base comprises an organic amine.

I-18. The system of any of I-1 to I-17, wherein the cleavage reactor comprises a heat exchanger for extracting heat from the reaction medium, such that the temperature of the reaction medium inside the cleavage reactor is maintained at a temperature Tcr, where 10≤Tcr≤120° C.

II-1. A system configured to separate a cyclohexylbenzene hydroperoxide cleavage reaction mixture comprising phenol, cyclohexanone, an amine salt, cyclohexylbenzene, and water, the system comprising:
(II-1A) a first fractionation column configured to receive at least a portion of the reaction mixture to produce a first lower effluent comprising the amine salt, and a first upper effluent comprising phenol, cyclohexanone and water;
(II-1B) a second fractionation column in fluid communication with the first fractionation column configured to receive at least a portion of the first upper effluent to produce a second lower effluent comprising phenol and cyclohexanone, and a second upper effluent comprising water;
(II-1C) a third fractionation column in fluid communication with the second fraction column configured to receive at least a portion of the second lower effluent and an extractive solvent to produce a third lower effluent comprising phenol and the extractive solvent, and a third upper effluent comprising at least 60 wt % of cyclohexanone, the percentage based on the total weight of the third upper effluent;
(II-1D) an optional fourth fractionation column in fluid communication with the third fractionation column configured to receive at least a portion of the third upper effluent to produce a fourth lower effluent comprising components having normal boiling points higher than that of cyclohexanone, and a fourth upper effluent comprising at least 90 wt % cyclohexanone, the percentage based on the total weight of the fourth upper effluent;
(II-1E) a fifth fractionation column in fluid communication with the third fractionation column configured to receive at least a portion of the third lower effluent to produce a fifth lower effluent comprising the extractive solvent, and a fifth upper effluent comprising at least 60 wt % of phenol, the percentage based on the total weight of the fifth upper effluent; and
(II-1F) a sixth fractionation column in fluid communication with the fifth fractionation column configured to receive at least a portion of the fifth upper effluent to produce a sixth bottom effluent comprising cyclohexylbenzene, and a sixth upper effluent comprising at least 90 wt % of phenol, the percentage based on the total weight of the sixth upper effluent.

II-2. The system of II-1, wherein the first fractionation column is configured to further produce a first middle effluent comprising cyclohexylbenzene.

II-3. The system of II-2, wherein the first middle effluent comprises at least 90 wt % of cyclohexylbenzene.

II-4. The system of II-3, wherein the first lower effluent comprises at least 80 wt % of the amine salt.

II-5. The system of any of II-1 to II-4, wherein the first lower effluent further comprises cyclohexylbenzene, and the system further comprises:
(II-1G) a seventh fractionation column in fluid communication with the first fractionation column configured to receive at least a portion of the first lower effluent to produce a seventh bottom effluent comprising the amine salt, and a seventh upper effluent comprising cyclohexylbenzene.

II-6. The system of any of II-1 to II-5, wherein the first fractionation column, the second fractionation column, the third fractionation column, and the fifth fractionation are configured to operate at an absolute pressure below 100 kPa.

II-7. The system of any of II-1 or II-6, wherein the fourth fractionation column, if present, and the sixth fractionation column are configured to operate at an absolute pressure higher than 100 kPa.

II-8. The system of any of II-1 to II-7, wherein at least one of the following conditions is met:

(II-8.1) the first fractionation column comprise a first reboiler in the vicinity of the bottom thereof providing heat to the fluid therein, and a first condenser in the vicinity of the top thereof providing a first reflux stream to the first fractionation column;

(II-8.2) the second fractionation column comprise a second reboiler in the vicinity of the bottom thereof providing heat to the fluid therein, and a second condenser in the vicinity of the top thereof providing a second reflux stream to the second fractionation column;

(II-8.3) the third fractionation column comprise a third reboiler in the vicinity of the bottom thereof providing heat to the fluid therein, and a third condenser in the vicinity of the top thereof providing a third reflux stream to the third fractionation column;

(II-8.4) the fourth fractionation column comprise a fourth reboiler in the vicinity of the bottom thereof providing heat to the fluid therein, and a fourth condenser in the vicinity of the top thereof providing a fourth reflux stream to the fourth fractionation column;

(II-8.5) the fifth fractionation column comprise a fifth reboiler in the vicinity of the bottom thereof providing heat to the fluid therein, and a fifth condenser in the vicinity of the top thereof providing a fifth reflux stream to the fifth fractionation column;

(II-8.6) the sixth fractionation column comprise a sixth reboiler in the vicinity of the bottom thereof providing heat to the fluid therein, and a sixth condenser in the vicinity of the top thereof providing a sixth reflux stream to the sixth fractionation column; and (II-8.7) the seventh fractionation column, if present, comprises a seventh reboiler in the vicinity of the bottom thereof providing heat to the fluid therein, and a seventh condenser in the vicinity of the top thereof providing a seventh reflux stream to the seventh fractionation column.

II-9. The system of any of II-1 to II-8, wherein:

the first fractionation column is configured to operate at a maximum temperature in the vicinity of the bottom thereof $Tmax1$, and a minimum temperature in the vicinity of the top thereof $Tmin1$;

the second fractionation column is configured to operate at a maximum temperature in the vicinity of the bottom thereof $Tmax2$, and a minimum temperature in the vicinity of the top thereof $Tmin2$;

the third fractionation column is configured to operate at a maximum temperature in the vicinity of the bottom thereof $Tmax3$, and a minimum temperature in the vicinity of the top thereof $Tmin3$;

the fourth fractionation column, if present, is configured to operate at a maximum temperature in the vicinity of the bottom thereof $Tmax4$, and a minimum temperature in the vicinity of the top thereof $Tmin4$;

the fifth fractionation column is configured to operate at a maximum temperature in the vicinity of the bottom thereof $Tmax5$, and a minimum temperature in the vicinity of the top thereof $Tmin5$;

the sixth fractionation column is configured to operate at a maximum temperature in the vicinity of the bottom thereof $Tmax6$, and a minimum temperature in the vicinity of the top thereof $Tmin6$;

the seventh fractionation column, if present, is configured to operate at a maximum temperature in the vicinity of the bottom thereof $Tmax7$, and a minimum temperature in the vicinity of the top thereof $Tmin7$;

and at least one of the following conditions is met:
(II-9.1) $Tmin6 > Tmax3$;
(II-9.2) $Tmin6 > Tmax5$;
(II-9.3) $Tmin6 > Tmax2$; and
(II-9.4) $Tmin7 > Tmax2$.

II-10. The system of II-9, wherein at least one of the following conditions is met:
(II-10.1) $Tmax1 > Tmax6 > Tmax5 > Tmax3 > Tmax2$;
(II-10.2) $Tmax1 > Tmax4$; and
(II-10.3) $Tmax1 > Tmax6$.

II-11. The system of any of II-1 to II-10, wherein at least one of the first, second, third, fourth, fifth or sixth upper effluents provides heat to a fluid fed into an upstream fractionation column.

II-12. The system of II-11, wherein at least one of the following conditions is met:

(II-12.1) a stream taken from a location in the vicinity of the top of the six fractionation column provides heat to a fluid fed into the third fractionation column;

(II-12.2) a stream taken from a location in the vicinity of the top of the six fractionation column provides heat to a fluid fed into the fifth fractionation column;

(II-12.3) a stream taken from a location in the vicinity of the top of the six fractionation column provides heat to a fluid fed into the first fractionation column; and (II-12.4) a stream taken from a location in the vicinity of the top of the fourth fractionation column provides heat to a fluid fed into the first fractionation column.

II-13. The system of II-12, wherein at least one of the following conditions is met:

(II-13.1) a stream taken from a location in the vicinity of the top of the six fractionation column provides heat to a fluid fed into the third fractionation column via the third reboiler;

(II-13.2) a stream taken from a location in the vicinity of the top of the six fractionation column provides heat to a fluid fed into the fifth fractionation column via the fifth reboiler;

(II-13.3) a stream taken from a location in the vicinity of the top of the six fractionation column provides heat to the reaction mixture fed into the first fractionation column; and (II-13.4) a stream taken from a location in the vicinity of the top of the fourth fractionation column provides heat to the reaction mixture fed into the first fractionation column.

II-14. The system of any of II-1 to II-13, wherein the extractive solvent comprises a glycol.

II-15. The system of II-14, wherein the extractive solvent comprises diethyleneglycol.

II-16. The system of any of II-1 to II-15, wherein the fifth fractionation column is in a further fluid communication with the third fractionation column through which at least part the extractive solvent contained in the fifth bottom effluent is recycled into the third fractionation column.

II-17. The system of any of II-1 to II-16, wherein the fourth fractionation column is in a further fluid communication with the first fractionation column through which at least part of the fourth lower effluent is recycled into the first fractionation column.

II-18. The system of any of II-1 to II-17, wherein the sixth fractionation column is in a further fluid communication with the first fractionation column through which at least part of the sixth lower effluent is recycled into the first fractionation column.

II-19. A system of any of II-9 to II-18, wherein at least one of the following conditions is met:
(II-19.1) $180° C. \leq Tmax1 \leq 300° C.$;
(II-19.2) $80° C. \leq Tmin1 \leq 150° C.$;
(II-19.3) $80° C. \leq Tmax2 \leq 180° C.$;
(II-19.4) $40° C. \leq Tmin2 \leq 100° C.$;
(II-19.5) $120° C. \leq Tmax3 \leq 220° C.$;
(II-19.6) $50° C. \leq Tmin3 \leq 150° C.$;

(II-19.7) 120° C.≤Tmax4≤300° C.;
(II-19.8) 150° C.≤Tmin4≤250° C.;
(II-19.9) 120° C.≤Tmax5≤250° C.;
(II-19.10) 80° C.≤Tmin5≤180° C.;
(II-19.11) 150° C.≤Tmax6≤300° C.;
(II-19.12) 120° C.≤Tmin6≤250° C.
(II-19.13) 150° C.≤Tmax7≤400° C.; and
(II-19.14) 120° C.≤Tmin7≤300° C.

III-1. A system for producing phenol and/or cyclohexanone, comprising a system of any of I-1 to I-18, and a system of any of II-1 to II-19.

IV-1. A process for producing phenol and/or cyclohexanone using a system according to any one of the preceding embodiments of I-1 to I-18.

IV-2. A process of IV-1, comprising the following steps:

(IV-1A) reacting a cyclohexylbenzene feed comprising an olefin with hydrogen in a hydrogenation reactor comprising a bed of hydrogenation to produce a hydrogenation effluent with a reduced concentration of the olefin compared to the feed;

(IV-1B) separating at least a portion of the hydrogenation effluent in a separation drum in fluid communication with the hydrogenation reactor to produce a lower drum effluent consisting essentially of a liquid, and an upper drum effluent consisting essentially of a gas;

(IV-1C) feeding into an oxidizing device comprising at least one bubble column reactor in fluid communication with the separation drum (i) at least a portion of the lower drum effluent, (ii) a stream of $O_2$-containing gas at a location in the vicinity of the bottom thereof, and (iii) a cyclic imide catalyst to produce a lower oxidation effluent comprising cyclohexylbenzene and cyclohexylbenzene hydroperoxide and an upper oxidation effluent;

(IV-1D) concentrating in a concentrator configured to operate under an absolute internal pressure of Pcon, where 133 Pa≤Pcon≤6666 Pa, in fluid communication with the oxidizing device at least a portion of the lower oxidation effluent, to produce a lower concentrator effluent comprising at least 30 wt % of cyclohexylbenzene hydroperoxide, the percentage based on the total weight of the lower concentrator effluent, and an upper concentrator effluent comprising at least 50 wt % of cyclohexylbenzene, the percentage based on the total weight of the upper concentrator effluent; and (IV-1E) feeding into a cleavage reactor comprising a vessel (i) at least a portion of the cyclohexylbenzene hydroperoxide in the lower concentrator effluent and (ii) a cleavage catalyst to produce a cleavage reaction effluent comprising phenol, cyclohexanone, and cyclohexylbenzene.

V-1. A process for producing phenol and/or cyclohexanone using a system according to any of the preceding embodiments II-1 to II-19.

V-2. The process of V-1, comprising the following steps:

(V-1A) fractionating in a first fractionation column at least a portion of the reaction mixture to produce a first lower effluent comprising the amine salt; a first middle effluent comprising cyclohexylbenzene, and a first upper effluent comprising phenol, cyclohexanone and water;

(V-1B) fractionating in a second fractionation column in fluid communication with the first fractionation column configured to receive at least a portion of the first upper effluent to produce a second lower effluent comprising phenol and cyclohexanone, and a second upper effluent comprising water;

(V-1C) fractionating in a third fractionation column in fluid communication with the second fraction column configured to receive at least a portion of the second lower effluent and an extractive solvent to produce a third lower effluent comprising phenol and the extractive solvent, and a third upper effluent comprising at least 60 wt % of cyclohexanone, the percentage based on the total weight of the third upper effluent;

(V-1D) fractionating in an optional fourth fractionation column in fluid communication with the third fractionation column configured to receive at least a portion of the third upper effluent to produce a fourth lower effluent comprising components having normal boiling points higher than that of cyclohexanone, and a fourth upper effluent comprising at least 90 wt % cyclohexanone, the percentage based on the total weight of the fourth upper effluent;

(V-1E) fractionating in a fifth fractionation column in fluid communication with the third fractionation column configured to receive at least a portion of the third lower effluent to produce a fifth lower effluent comprising the extractive solvent, and a fifth upper effluent comprising at least 60 wt % of phenol, the percentage based on the total weight of the fifth upper effluent; and (V-1F) fractionating in a sixth fractionation column in fluid communication with the fifth fractionation column configured to receive at least a portion of the fifth upper effluent to produce a sixth bottom effluent comprising cyclohexylbenzene, and a sixth upper effluent comprising at least 90 wt % of phenol, the percentage based on the total weight of the sixth upper effluent.

VI-1. A process for producing phenol and/or cyclohexanone using a system of III-1.

VII-1. A process for producing phenol and/or cyclohexanone, comprising a process of IV-1 or IV-2, and a process of V-1 or V-2.

The invention claimed is:

1. A system for producing phenol and/or cyclohexanone from cyclohexylbenzene, the system comprising:
   (A) a hydrogenation reactor comprising a bed of hydrogenation catalyst, configured to receive a cyclohexylbenzene feed comprising an olefin and hydrogen and to produce a hydrogenation effluent with a reduced concentration of the olefin compared to the feed;
   (B) a separation drum in fluid communication with the hydrogenation reactor configured to receive at least a portion of the hydrogenation effluent and to produce a lower drum effluent consisting essentially of a liquid, and an upper drum effluent consisting essentially of a gas;
   (C) an oxidizing device comprising at least one bubble column reactor in fluid communication with the separation drum configured to receive (i) at least a portion of the lower drum effluent, (ii) a stream of $O_2$-containing gas fed into the bubble column reactor at a location in the vicinity of the bottom thereof, and (iii) a cyclic imide catalyst, and to produce a lower oxidation effluent comprising cyclohexylbenzene and cyclohexylbenzene hydroperoxide and an upper oxidation effluent;
   (D) a concentrator configured to operate under an absolute internal pressure of Pcon, where 133 Pa≤Pcon≤6666 Pa, in fluid communication with the oxidizing device configured to receive at least a portion of the lower oxidation effluent and to produce a lower concentrator effluent comprising at least 30 wt % of cyclohexylbenzene hydroperoxide, the percentage based on the total weight of the lower concentrator effluent, and an upper concentrator effluent comprising at least 50 wt % of cyclohexylbenzene, the percentage based on the total weight of the upper concentrator effluent; and
   (E) a cleavage reactor comprising a vessel configured to receive (i) at least a portion of the cyclohexylbenzene hydroperoxide in the lower concentrator effluent and (ii)

a cleavage catalyst and to produce a cleavage reaction effluent comprising phenol, cyclohexanone, and cyclohexylbenzene.

2. The system of claim 1, the system further comprising:
(F) a first fractionation column configured to separate at least a portion of the cyclohexylbenzene in the cleavage reaction effluent further in fluid communication with the hydrogenation reactor by which at least a portion of the separated cyclohexylbenzene is recycled to the hydrogenation reactor.

3. The system of claim 1, wherein the concentrator is in further fluid communication with the hydrogenation reactor through which at least a portion of the cyclohexylbenzene in the upper concentrator effluent is recycled to the hydrogenation reactor.

4. The system of claim 1, wherein the separation drum is in further fluid communication with a combustor through which at least a portion of the upper drum effluent is sent to the combustor.

5. The system of claim 1, wherein the hydrogenation reactor is configured to operate at a temperature of Thr and a pressure Phr, where 50° C.≤Thr≤150° C., and 150 kPa≤Phr≤1850 kPa.

6. The system of claim 1, wherein the separation drum is configured to operate at a temperature of Tsd, where 50° C.≤Tsd≤150° C.

7. The system of claim 6, wherein the separation drum is configured to operate at a temperature no less than Thr−20° C., where Thr is the operating temperature of the hydrogenation reactor.

8. The system of claim 1, wherein the concentrator is configured to operate at a temperature of Tcon, where 50° C.≤Tcon≤150° C.

9. The system of claim 1, where the concentrator comprises a falling film evaporator.

10. The system of claim 2, wherein:
the cleavage catalyst comprises a liquid acid;
the system further comprises, between the cleavage reactor and the first fractionation column, a neutralization reactor configured to receive at least a portion of the cleavage reaction effluent and a base and to produce a cleavage reaction mixture having a reduced concentration of the cleavage catalyst compared to the cleavage reactor effluent,
at least a portion of the cleavage reaction mixture is fed into the first fractionation column.

11. The system of claim 1, further comprising:
(1) a first fractionation column configured to receive at least a portion of a cleavage reaction mixture comprising phenol, cyclohexanone, an amine salt, cyclohexylbenzene, and water, and to produce a first lower effluent comprising the amine salt, and a first upper effluent comprising phenol, cyclohexanone and water;
(2) a second fractionation column in fluid communication with the first fractionation column configured to receive at least a portion of the first upper effluent to produce a second lower effluent comprising phenol and cyclohexanone, and a second upper effluent comprising water;
(3) a third fractionation column in fluid communication with the second fraction column configured to receive at least a portion of the second lower effluent and an extractive solvent to produce a third lower effluent comprising phenol and the extractive solvent, and a third upper effluent comprising at least 60 wt % of cyclohexanone, the percentage based on the total weight of the third upper effluent;

(4) an optional fourth fractionation column in fluid communication with the third fractionation column configured to receive at least a portion of the third upper effluent to produce a fourth lower effluent comprising components having normal boiling points higher than that of cyclohexanone, and a fourth upper effluent comprising at least 90 wt % cyclohexanone, the percentage based on the total weight of the fourth upper effluent;
(5) a fifth fractionation column in fluid communication with the third fractionation column configured to receive at least a portion of the third lower effluent to produce a fifth lower effluent comprising the extractive solvent, and a fifth upper effluent comprising at least 60 wt % of phenol, the percentage based on the total weight of the fifth upper effluent; and
(6) a sixth fractionation column in fluid communication with the fifth fractionation column configured to receive at least a portion of the fifth upper effluent to produce a sixth bottom effluent comprising cyclohexylbenzene, and a sixth upper effluent comprising at least 90 wt % of phenol, the percentage based on the total weight of the sixth upper effluent.

12. The system of claim 11, wherein the first fractionation column is configured to further produce a first middle effluent comprising cyclohexylbenzene.

13. The system of claim 11, wherein the first lower effluent further comprises cyclohexylbenzene, and the system further comprises:
(7) a seventh fractionation column in fluid communication with the first fractionation column configured to receive at least a portion of the first lower effluent to produce a seventh bottom effluent comprising the amine salt, and a seventh upper effluent comprising cyclohexylbenzene.

14. The system of claim 11, wherein the first fractionation column, the second fractionation column, the third fractionation column, the fifth fractionation column, and the seventh fractionation column, if present, are configured to operate under an absolute pressure below 100 kPa.

15. The system of claim 11, wherein the fourth fractionation column, if present, and the sixth fractionation column are configured to operate at an absolute pressure higher than 100 kPa.

16. The system of claim 11, wherein at least one of the following conditions is met:
(1) the first fractionation column comprises a first reboiler in the vicinity of the bottom thereof providing heat to the fluid therein, and a first condenser in the vicinity of the top thereof providing a first reflux stream to the first fractionation column;
(2) the second fractionation column comprises a second reboiler in the vicinity of the bottom thereof providing heat to the fluid therein, and a second condenser in the vicinity of the top thereof providing a second reflux stream to the second fractionation column;
(3) the third fractionation column comprises a third reboiler in the vicinity of the bottom thereof providing heat to the fluid therein, and a third condenser in the vicinity of the top thereof providing a third reflux stream to the third fractionation column;
(4) the fourth fractionation column, if present, comprises a fourth reboiler in the vicinity of the bottom thereof providing heat to the fluid therein, and a fourth condenser in the vicinity of the top thereof providing a fourth reflux stream to the fourth fractionation column;
(5) the fifth fractionation column comprises a fifth reboiler in the vicinity of the bottom thereof providing heat to the fluid therein, and a fifth condenser in the vicinity of the top thereof providing a fifth reflux stream to the fifth fractionation column;

(6) the sixth fractionation column comprises a sixth reboiler in the vicinity of the bottom thereof providing heat to the fluid therein, and a sixth condenser in the vicinity of the top thereof providing a sixth reflux stream to the sixth fractionation column; and (7) the seventh fractionation column, if present, comprises a seventh reboiler in the vicinity of the bottom thereof providing heat to the fluid therein, and a seventh condenser in the vicinity of the top thereof providing a seventh reflux stream to the seventh fractionation column.

17. The system of claim 11, wherein:

the first fractionation column is configured to operate with a maximum temperature in the vicinity of the bottom thereof Tmax1, and a minimum temperature in the vicinity of the top thereof Tmin1;

the second fractionation column is configured to operate at a maximum temperature in the vicinity of the bottom thereof Tmax2, and a minimum temperature in the vicinity of the top thereof Tmin2;

the third fractionation column is configured to operate at a maximum temperature in the vicinity of the bottom thereof Tmax3, and a minimum temperature in the vicinity of the top thereof Tmin3;

the fourth fractionation column, if present, is configured to operate at a maximum temperature in the vicinity of the bottom thereof Tmax4, and a minimum temperature in the vicinity of the top thereof Tmin4;

the fifth fractionation column is configured to operate at a maximum temperature in the vicinity of the bottom thereof Tmax5, and a minimum temperature in the vicinity of the top thereof Tmin5;

the sixth fractionation column is configured to operate at a maximum temperature in the vicinity of the bottom thereof Tmax6, and a minimum temperature in the vicinity of the top thereof Tmin6;

the seventh fractionation column, if present, is configured to operate at a maximum temperature in the vicinity of the bottom thereof Tmax7, and a minimum temperature in the vicinity of the top thereof Tmin7; and at least one of the following conditions is met:
(1) Tmin6>Tmax3;
(2) Tmin6>Tmax5;
(3) Tmin6>Tmax2; and
(4) Tmin7>Tmax2.

18. The system of claim 17, wherein at least one of the following conditions is met:
(1) Tmax1>Tmax6>Tmax5>Tmax3>Tmax2;
(2) Tmax1>Tmax4; and
(3) Tmax1>Tmax6.

19. The system of claim 11, wherein at least one of the first, second, third, fourth, fifth or sixth upper effluents provides heat to a fluid fed into an upstream fractionation column.

20. The system of claim 19, wherein at least one of the following conditions is met:
(1) a stream taken from a location in the vicinity of the top of the sixth fractionation column provides heat to a fluid fed into the third fractionation column;
(2) a stream taken from a location in the vicinity of the top of the sixth fractionation column provides heat to a fluid fed into the fifth fractionation column;
(3) a stream taken from a location in the vicinity of the top of the six fractionation column provides heat to a fluid fed into the first fractionation column; and
(4) a stream taken from a location in the vicinity of the top of the fourth fractionation column provides heat to a fluid fed into the first fractionation column.

21. The system of claim 20, wherein at least one of the following conditions is met:
(1) a stream taken from a location in the vicinity of the top of the sixth fractionation column provides heat to a fluid fed into the third fractionation column via the third reboiler;
(2) a stream taken from a location in the vicinity of the top of the sixth fractionation column provides heat to a fluid fed into the fifth fractionation column via the fifth reboiler;
(3) a stream taken from a location in the vicinity of the top of the six fractionation column provides heat to the reaction mixture fed into the first fractionation column; and
(4) a stream taken from a location in the vicinity of the top of the fourth fractionation column provides heat to the reaction mixture fed into the first fractionation column.

22. A process for producing phenol and/or cyclohexanone using a system according to claim 1.

23. A process for producing phenol and/or cyclohexanone using a system according to claim 11.

* * * * *